United States Patent
Vazquez (10) Patent No.: US 11,998,797 B2
(45) Date of Patent: Jun. 4, 2024

(54) EXERCISE DEVICE

(71) Applicant: Norma Vazquez, Santa Ana, CA (US)

(72) Inventor: Norma Vazquez, Santa Ana, CA (US)

( * ) Notice: Subject to any disclaimer, the term of this patent is extended or adjusted under 35 U.S.C. 154(b) by 208 days.

(21) Appl. No.: 17/678,755

(22) Filed: Feb. 23, 2022

(65) Prior Publication Data

US 2023/0264074 A1 Aug. 24, 2023

(51) Int. Cl.
| | | |
|---|---|---|
| *A63B 23/035* | (2006.01) | |
| *A61F 7/00* | (2006.01) | |
| *A63B 21/00* | (2006.01) | |
| *A63B 21/04* | (2006.01) | |
| *A63B 23/08* | (2006.01) | |
| *A63B 23/12* | (2006.01) | |
| *A63B 71/00* | (2006.01) | |

(52) U.S. Cl.
CPC ........ *A63B 23/0355* (2013.01); *A61F 7/007* (2013.01); *A63B 21/0421* (2013.01); *A63B 21/4011* (2015.10); *A63B 21/4034* (2015.10); *A63B 21/4035* (2015.10); *A63B 21/4047* (2015.10); *A63B 23/03541* (2013.01); *A63B 23/08* (2013.01); *A63B 23/1245* (2013.01); *A63B 71/0054* (2013.01); *A61F 2007/0022* (2013.01); *A61F 2007/0036* (2013.01); *A61F 2007/0045* (2013.01); *A63B 2208/0233* (2013.01); *A63B 2225/64* (2013.01)

(58) Field of Classification Search
None
See application file for complete search history.

(56) References Cited

U.S. PATENT DOCUMENTS

| | | | | |
|---|---|---|---|---|
| 5,044,633 A | * | 9/1991 | Rice | A63B 21/055 |
| | | | | 482/130 |
| 5,176,601 A | * | 1/1993 | Reynolds | A63B 23/12 |
| | | | | 482/121 |
| 5,234,394 A | | 8/1993 | Wilkinson | |
| 5,324,247 A | * | 6/1994 | Lepley | A63B 21/4033 |
| | | | | 482/136 |
| 7,276,018 B2 | * | 10/2007 | Studdard | A63B 21/02 |
| | | | | 482/121 |

(Continued)

FOREIGN PATENT DOCUMENTS

| | | | |
|---|---|---|---|
| KR | 0179437 | * | 4/1999 |
| KR | 0179437 B1 | * | 4/1999 |

(Continued)

*Primary Examiner* — Shila Jalalzadeh Abyaneh (57) ABSTRACT

An exercise device for seated exercising and heat therapy includes a chair, to which a plurality of biasers is operationally engaged. A pair of footrests and a pair of handrests are operationally engaged to the chair. Each footrest and each handrest is engageable to an associated foot and an associated hand of the user, respectively. The footrest is operationally engaged to a respective biaser so that the respective biaser is positioned to resist movement of the footrest relative to the chair. The handrest is operationally engaged to a respective biaser so that the respective biaser is positioned to resist movement of the handrest relative to the chair. The footrests and the handrests thus are useful in exercising feet and hands of the user, respectively. A plurality of heating elements, which is engaged to the chair, the footrests, and the handrests, can warm an abdomen and joints of the user.

13 Claims, 7 Drawing Sheets

(56) References Cited

U.S. PATENT DOCUMENTS

| | | | |
|---|---|---|---|
| 7,993,247 | B1 | 8/2011 | Eschenbach |
| 8,864,221 | B1 | 10/2014 | Delvilla |
| 8,905,906 | B2 | 12/2014 | Man |
| 11,583,719 | B2 * | 2/2023 | Weisz ................ A63B 21/0414 |
| 2003/0073552 | A1 * | 4/2003 | Knight ................... A47C 9/002 |
| | | | 482/148 |
| 2004/0152572 | A1 * | 8/2004 | Reitz ................. A63B 21/1609 |
| | | | 482/142 |
| 2008/0132383 | A1 * | 6/2008 | Einav ................ A61H 23/0263 |
| | | | 482/8 |
| 2009/0233773 | A1 | 9/2009 | Cardey |
| 2016/0066691 | A1 | 3/2016 | Patnaik |
| 2016/0324713 | A1 * | 11/2016 | Halperin ............. A61H 1/0262 |
| 2020/0260873 | A1 | 8/2020 | Flanagan |

FOREIGN PATENT DOCUMENTS

| | | | |
|---|---|---|---|
| KR | 20040017882 | * | 3/2004 |
| KR | 20040017882 A | * | 3/2004 |
| KR | 20180076299 A | * | 7/2018 |

* cited by examiner

FIG. 7

EXERCISE DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to exercise devices and more particularly pertains to a new exercise device for seated exercising and heat therapy. The present invention discloses an exercise device comprising a chair having footrests and handrests for exercising a user's limbs in combination with integral heating elements.

(2) Description of Related Art Including Information Disclosed Under 37 CFR 1.97 and 1.98

The prior art relates to exercise devices. The prior art discloses a variety of chairs useful in exercising, along with chairs that have integral heating elements. What is lacking in the prior art is an exercise device comprising a chair having footrests and handrests for exercising a user's limbs in combination with integral heating elements.

BRIEF SUMMARY OF THE INVENTION

An embodiment of the disclosure meets the needs presented above by generally comprising a chair, to which a plurality of biasers is operationally engaged. A pair of footrests is operationally engaged to the chair. Each footrest is configured to engage an associated foot of the user. The footrest is operationally engaged to a respective biaser so that the respective biaser is positioned to resist movement of the footrest relative to the chair. The footrests thus are configured to exercise feet of the user. A pair of handrests is operationally engaged to the chair. Each handrest is configured to engage an associated hand of the user. The handrest is operationally engaged to a respective biaser so that the respective biaser is positioned to resist movement of the handrest relative to the chair. The handrests thus are configured to exercise hands of the user. A plurality of heating elements is engaged to the chair, the footrests, and the handrests. The heating elements are configured to warm an abdomen and joints of the user.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

With reference now to the drawings, and in particular to FIGS. 1 through 7 thereof, a new exercise device embodying the principles and concepts of an embodiment of the disclosure and generally designated by the reference numeral 10 will be described.

As best illustrated in FIGS. 1 through 7, the exercise device 10 generally comprises a chair 12, to which a plurality of biasers 14 is operationally engaged. Each biaser 14 may comprise a spring 16, or other biasing element, such as, but not limited to, elastic bands, weighted pulleys, and the like.

Figure 1:
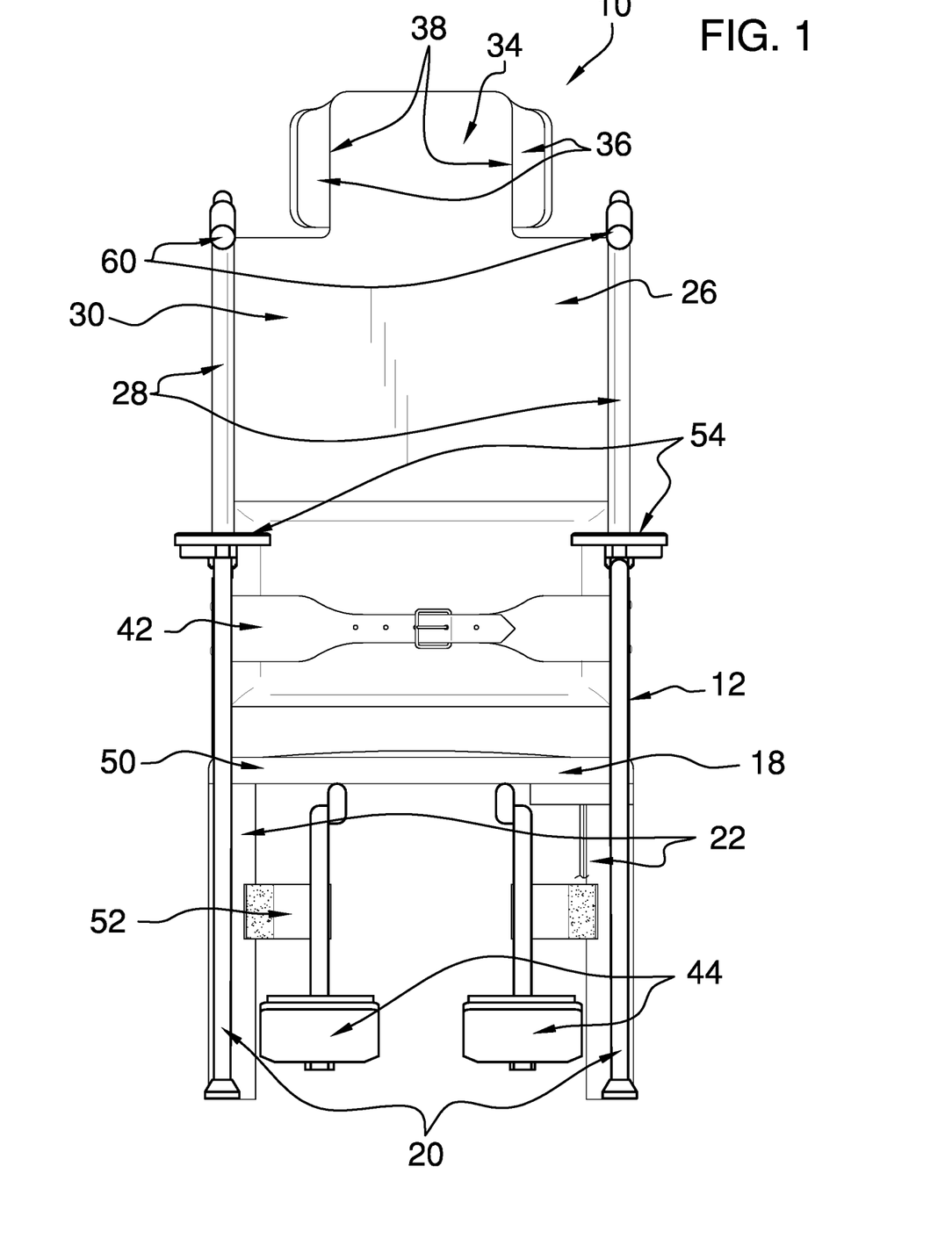
FIG. 1 is a front view of an exercise device according to an embodiment of the disclosure.
Figure 2:
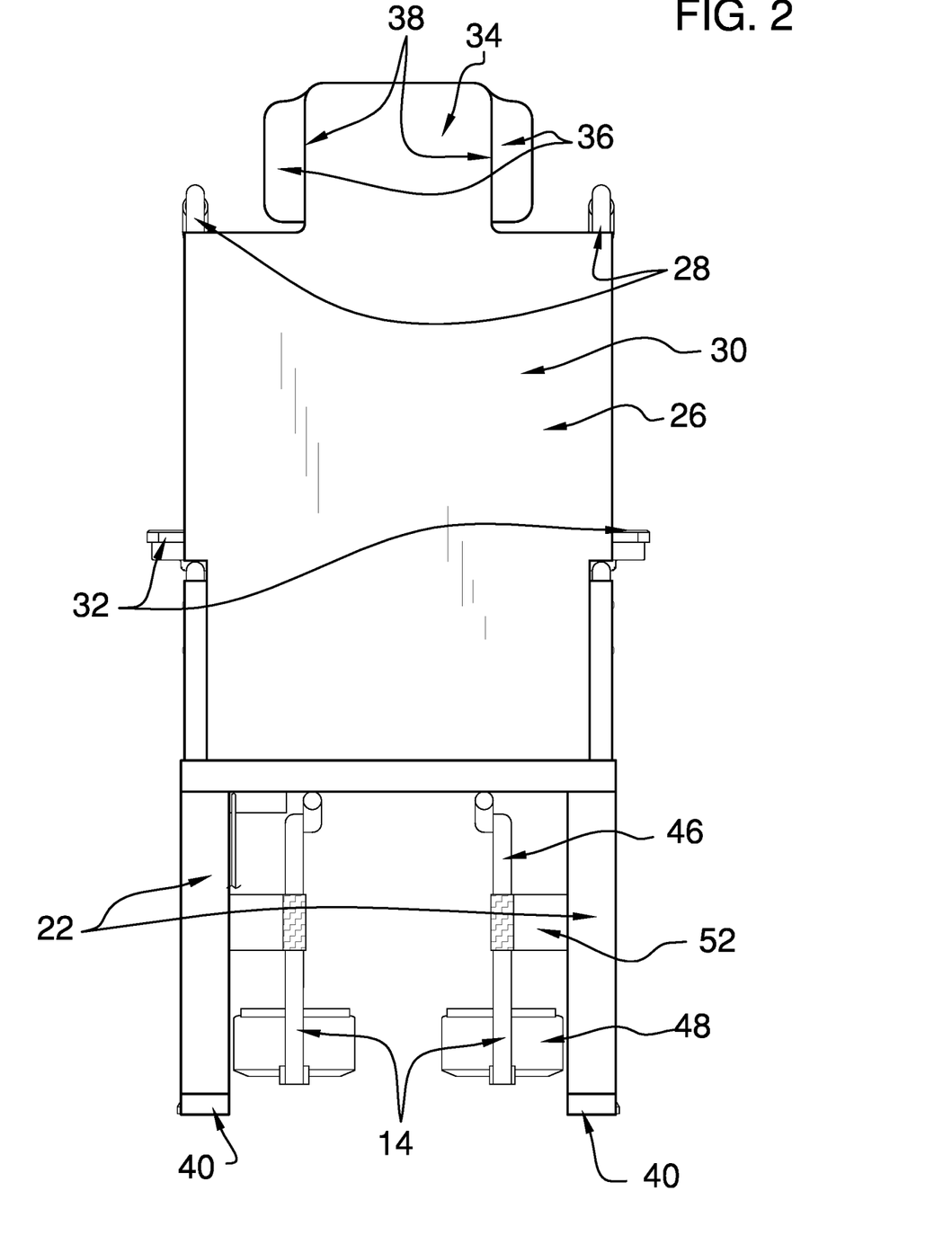
FIG. 2 is a rear view of an embodiment of the disclosure.
Figure 3:
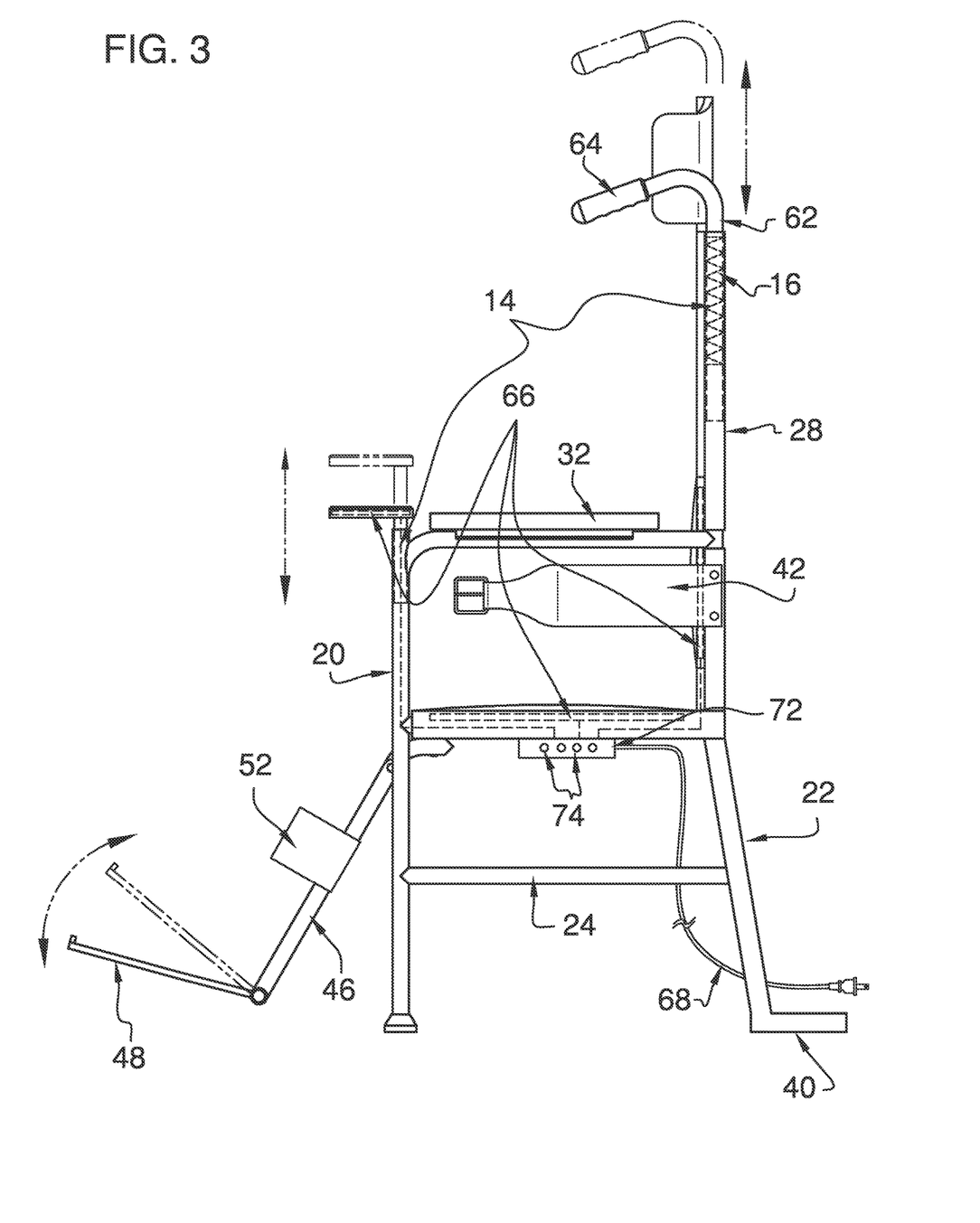
FIG. 3 is a side view of an embodiment of the disclosure.
Figure 4:
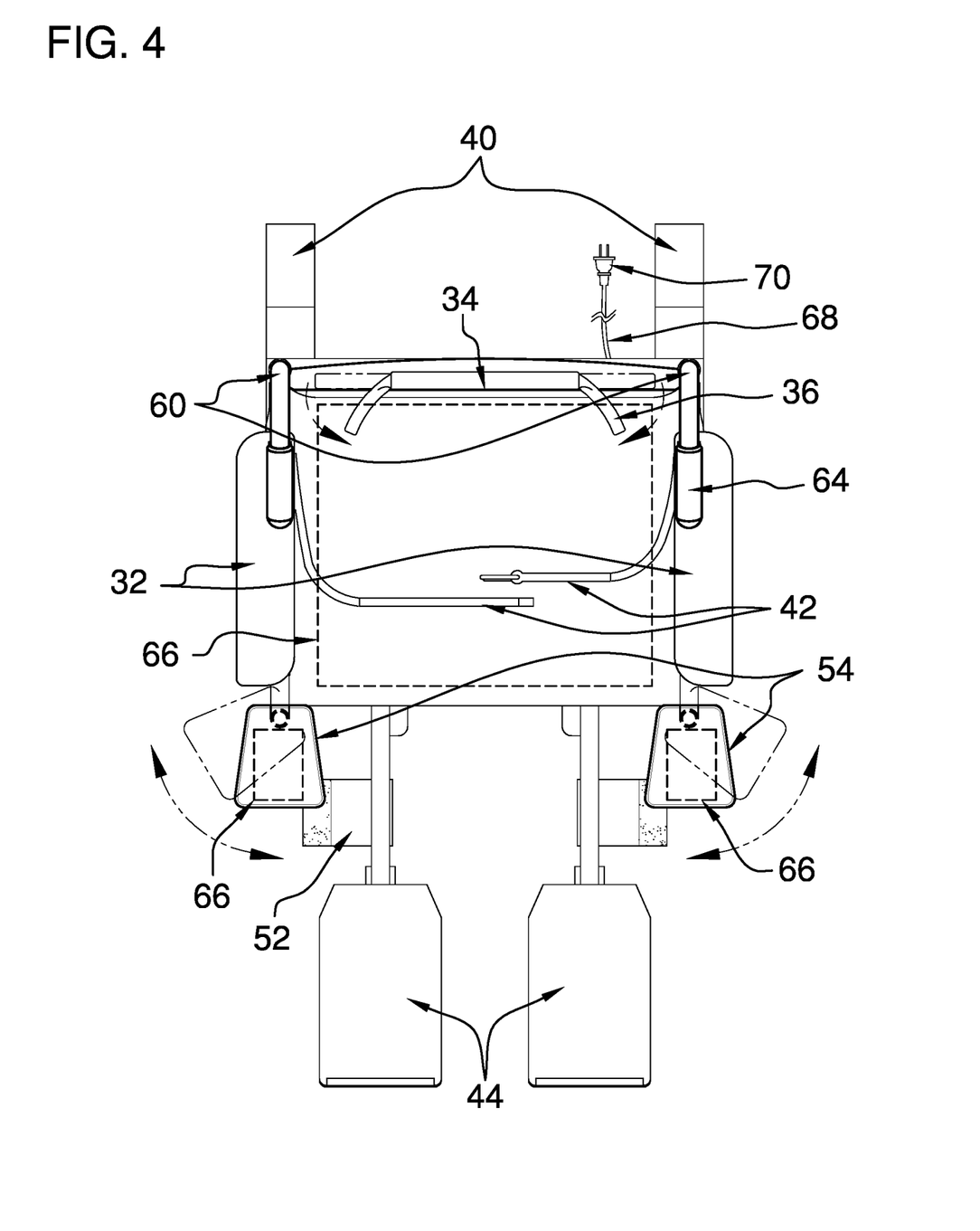
FIG. 4 is a top view of an embodiment of the disclosure.

The chair 12 may comprise a seat 18, a pair of front legs 20, and a pair of rear legs 22. The front legs 20 and the rear legs 22 are engaged to and extend from the seat 18. The front legs 20 and the rear legs 22 are configured to support the seat 18 on a substantially horizontal surface so that the seat 18 is configured to seat the user. As shown in FIG. 3, the front legs 20 extend past the seat 18. Each of a pair of crossbeams 24 is engaged to and extends between a respective rear leg 22 and an associated front leg 20. The crossbeams 24 stabilize the chair 12. A backrest 26 is engaged to and extends from the seat 18 proximate to the rear legs 22. The backrest 26 is configured to support a back of the user. The backrest 26 may comprise a pair of opposing side tubes 28 and a back panel 30. Each opposing side tube 28 is engaged to and extends from a respective rear leg 22. The back panel 30 is engaged to and extends between the opposing side tubes 28.

Each of a pair of armrests 32 is engaged to and extends between a respective front leg 20 and an associated opposing side tube 28.

A headrest 34 is engaged to the backrest 26 distal from the seat 18 and is configured to support a head of the user. Each of a pair of panels 36 is hingedly engaged to a respective opposed edge 38 of the headrest 34 so that the pair of panels 36 is selectively hingable into abutment with the head of the user, thereby providing additional support to the head of the user.

Each of a pair of extensions 40 is engaged to a respective rear leg 22 distal from the seat 18. The extension 40 extends opposingly from the respective rear leg 22 relative to the seat 18. The extensions 40 thus are configured to engage the substantially horizontal surface to resist tilting of the chair 12. A safety belt 42 is engaged to the backrest 26 and is configured to be positioned around the abdomen of the user so that the user is engaged to the chair 12. The safety belt 42 may be securable around the abdomen of the user by means well known to those skilled in the art of safety belts 42, such as, but not limited to, buckles, hook and loop fasteners, and the like.

Figure 5:
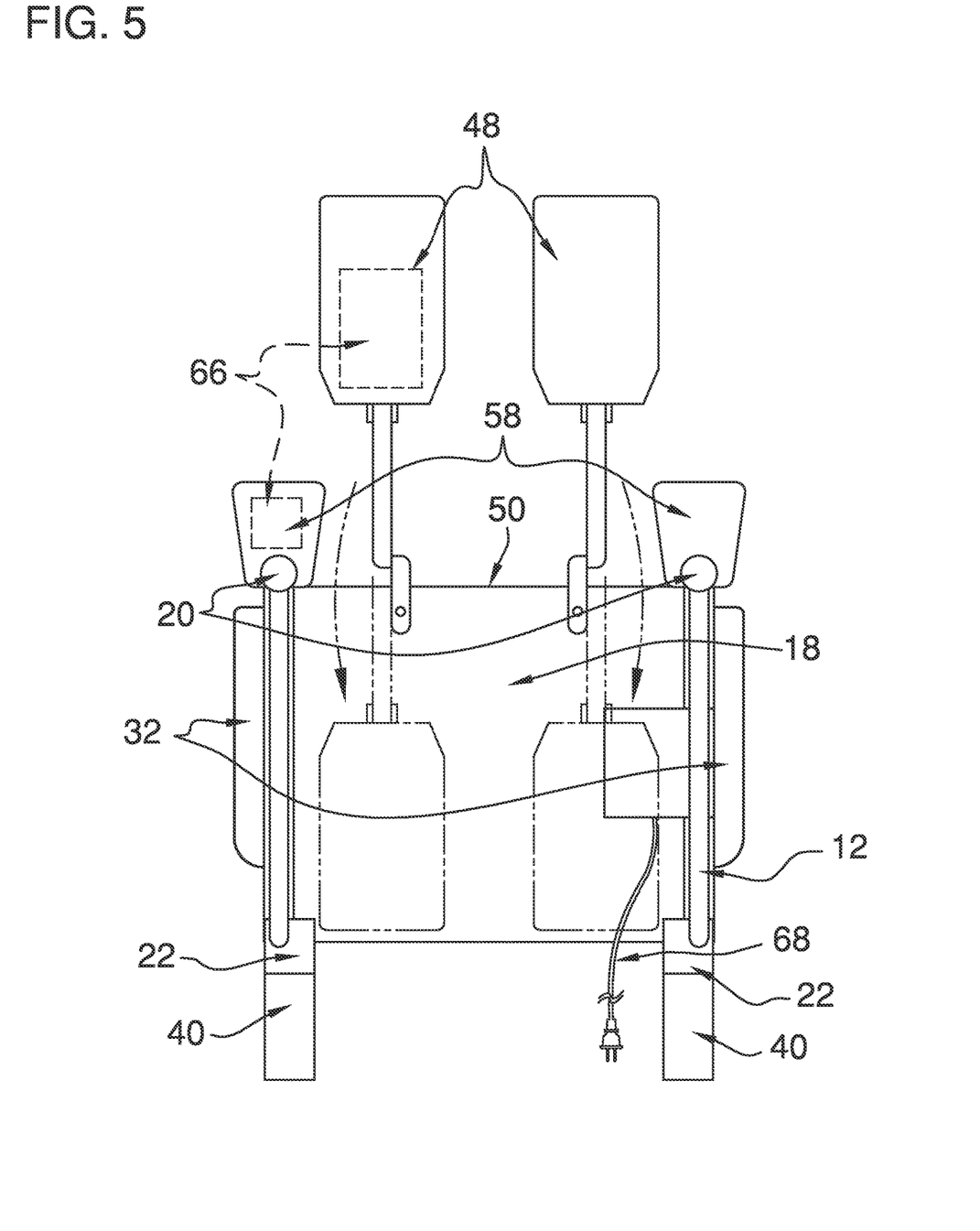
FIG. 5 is a bottom view of an embodiment of the disclosure.
Figure 6:
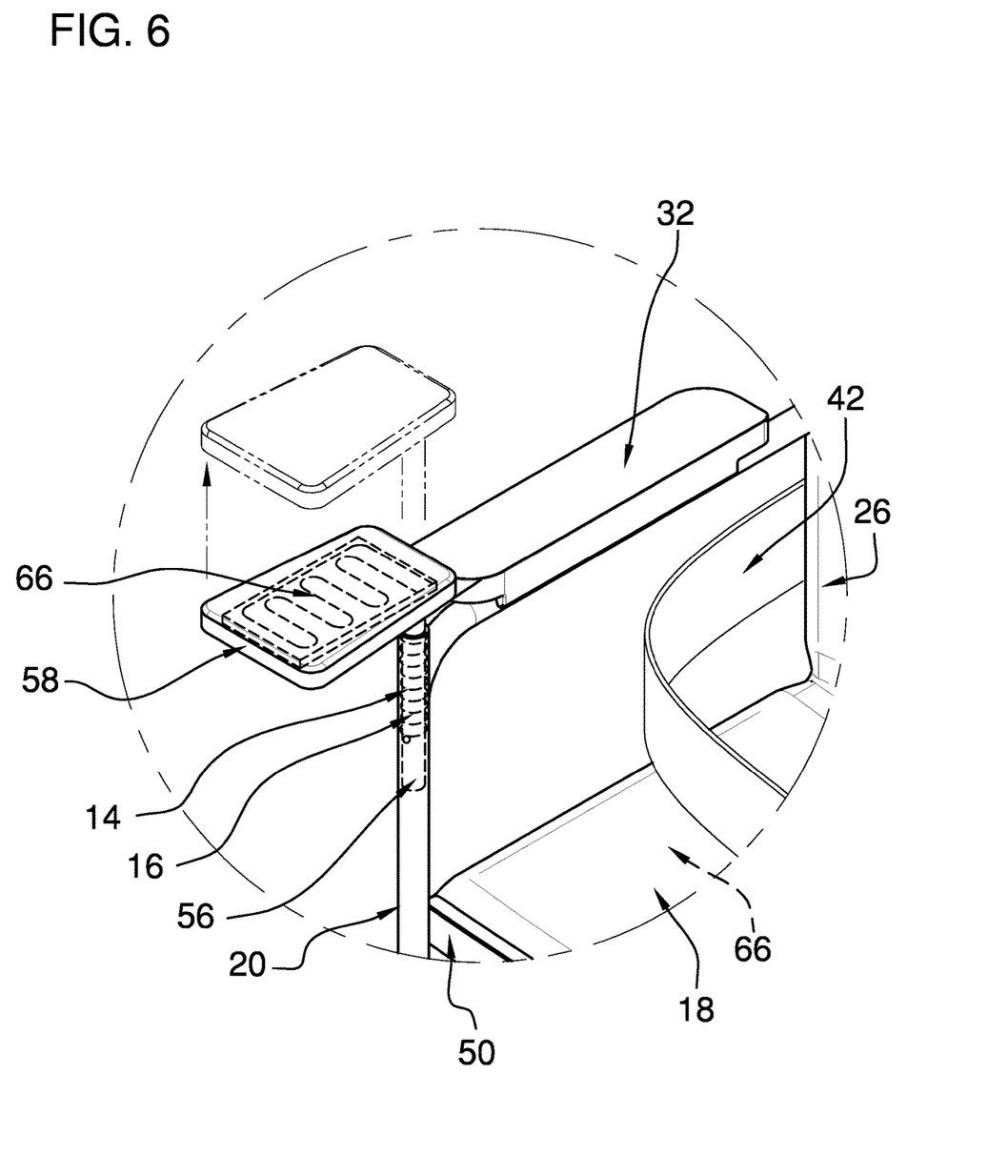
FIG. 6 is a detail view of an embodiment of the disclosure.

A pair of footrests 44 is operationally engaged to the chair 12. Each footrest 44 is configured to engage an associated foot of the user. The footrest 44 is operationally engaged to a respective biaser 14 so that the respective biaser 14 is positioned to resist movement of the footrest 44 relative to the chair 12. The footrests 44 thus are configured to exercise feet of the user. The footrests 44 may be hingedly engaged to the seat 18, as shown in FIG. 5. The pair of footrests 44 is selectively positionable in a stowed configuration, as shown in FIG. 5 wherein the footrests 44 are positioned below the seat 18, and a deployed configuration, wherein the footrests 44 extend transversely from the seat 18.

Each footrest 44 comprises a foot rod 46 and a footpad 48. The foot rod 46 is engaged to and extends from a front edge 50 of the seat 18. The footpad 48 is hingedly engaged to the foot rod 46 distal from the seat 18. A respective spring 16 is positioned in and is engaged to the foot rod 46. The respective spring 16 is operationally engaged to the footpad 48 so that the respective spring 16 is tensioned as the footpad 48 is hinged relative to the foot rod 46. The present invention anticipates a strap 52 engaged to the foot rod 46 and configured to be positioned around an associated leg of the user so that the associated leg is engaged to the foot rod 46. The strap 52 may be securable around the associated leg of the user by means well known to those skilled in the art of strap connectors, such as, but not limited to, hook and loop fasteners, buckles, and the like.

A pair of handrests 54 is operationally engaged to the chair 12. Each handrest 54 is configured to engage an associated hand of the user. The handrest 54 is operationally engaged to a respective biaser 14 so that the respective biaser 14 is positioned to resist movement of the handrest 54 relative to the chair 12. The handrests 54 thus are configured to exercise hands of the user. The handrest 54 comprises a hand rod 56 and a handpad 58. The hand rod 56 is slidably engaged to and selectively extensible from a respective front leg 20 of the chair 12. The handpad 58 is engaged to the hand rod 56. A respective spring 16 is positioned in and is engaged to the respective front leg 20. The respective spring 16 is operationally engaged to the hand rod 56.

A pair of press bars 60 is operationally engaged to and is selectively extensible from the chair 12. Each press bar 60 is operationally engaged to a respective biaser 14 so that the respective biaser 14 is positioned to resist movement of the press bar 60 relative to the chair 12. The press bars 60 thus are configured to exercise arms and shoulders of the user. As shown in FIG. 3, the press bar 60 comprises a press rod 62 and a handle 64. The press rod 62 is slidably engaged to and is selectively extensible from a respective opposing side tube 28 of the backrest 26. The handle 64 is engaged to and extends arcuately from the press rod 62 so that the handle 64 is positioned over an associated shoulder of the user. A respective spring 16 is positioned in and is engaged to the respective opposing side tube 28. The respective spring 16 is operationally engaged to the press rod 62.

A plurality of heating elements 66 is engaged to the chair 12, the footrests 44, and the handrests 54. The heating elements 66 are configured to warm the abdomen and joints of the user. As shown in FIG. 3, heating elements 66 are positioned in each handpad 58, each footpad 48, the seat 18, and the backrest 26. The present invention also anticipates a heating element 66 being positioned in the safety belt 42.

A power cord 68 is engaged to and extends from the chair 12. The power cord 68 is operationally engaged to the plurality of heating elements 66. A plug 70 of the power cord 68 is configured to be selectively engaged to an outlet to operationally engage the plurality of heating elements 66 to a source of electrical current. A controller 72 is engaged to the chair 12 and is operationally engaged to the power cord 68 and the plurality of heating elements 66. The controller 72 is positioned to selectively and operationally engage a respective heating element 66 to the power cord 68 to power the respective heating element 66. As shown in FIG. 3, the controller 72 may comprise a plurality of switches 74, with each switch 74 being operationally engaged to a respective heating element 66.

Figure 7:
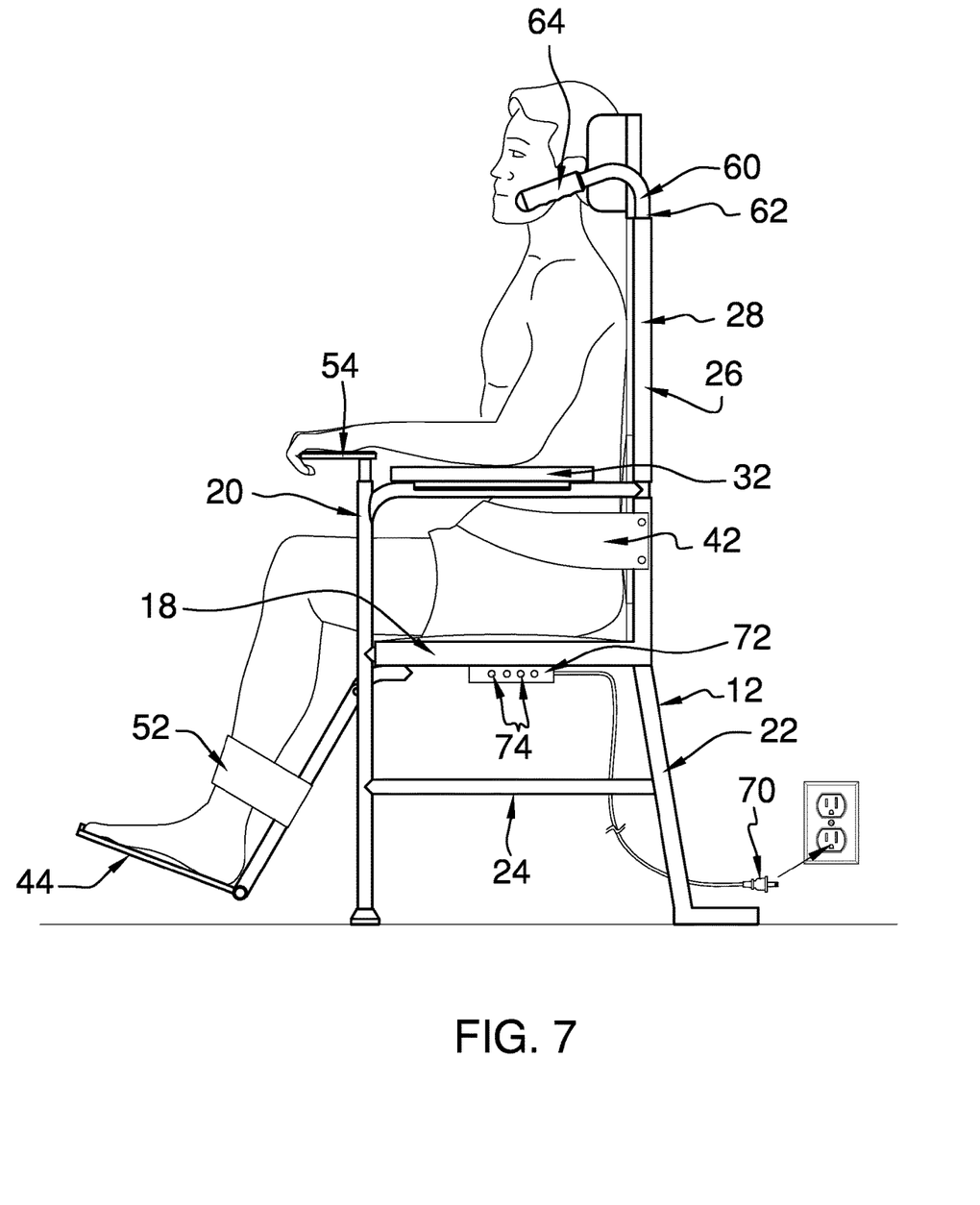
FIG. 7 is an in-use view of an embodiment of the disclosure.

In use, the user is positioned on the seat 18 and the safety belt 42 is secured around the abdomen of the user. The feet and hands of the user are positioned on the footpads 48 and handpads 58, respectively. The user then can perform resistance exercises by moving the footpads 48 and handpads 58 relative to the chair 12, with the biasers 14 providing resistance and stretching. The heating elements 66 can be engaged to warm the joints and the abdomen of the user, thereby providing relief from joint pain and promoting more complete bowel movements. The present invention is anticipated to be useful to elderly users who still wish to stretch and to exercise.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. An exercise device comprising:
   a chair;
   a plurality of biasers operationally engaged to the chair;
   a pair of footrests operationally engaged to the chair, each footrest being configured for engaging an associated foot of the user, the footrest being operationally engaged to a respective biaser, such that the respective biaser is positioned for resisting movement of the footrest relative to the chair, wherein the footrests are configured for exercising feet of the user;
   a pair of handrests operationally engaged to the chair, each handrest being configured for engaging an associated hand of the user, the handrest being operationally engaged to a respective biaser, such that the respective biaser is positioned for resisting movement of the handrest relative to the chair, wherein the handrests are configured for exercising hands of the user;
   a plurality of heating elements engaged to the chair, the footrests, and the handrests, wherein the heating elements are configured for warming an abdomen and joints of the user;
   wherein the chair comprises:
      a seat,
      a pair of front legs and a pair of rear legs engaged to and extending from the seat, wherein the front legs and the rear legs are configured for supporting the seat on a substantially horizontal surface, wherein the seat is configured for seating the user,
      a pair of crossbeams, each crossbeam being engaged to and extending between a respective rear leg and an associated front leg, and
      a backrest engaged to and extending from the seat proximate to the rear legs, wherein the backrest is configured for supporting a back of the user;
   wherein the backrest comprises:
      a pair of opposing side tubes, each opposing side tube being engaged to and extending from a respective rear leg, and
      a back panel engaged to and extending between the opposing side tubes:
   wherein each Maser comprises a spring;
   wherein the front legs extend past the seat; and
   wherein the handrest comprises:
      a hand rod slidably engaged to and selectively extensible from a respective front leg of the chair;
      a handpad engaged to the hand rod, and
      a respective biaser being positioned in and engaged to the respective front leg, the respective biaser being operationally engaged to the hand rod.

2. The exercise device of claim 1, wherein each footrest comprises:
   a foot rod engaged to and extending from a front edge of the seat; and
   a footpad hingedly engaged to the foot rod distal from the seat.

3. The exercise device of claim 2, further including a strap engaged to the foot rod and being configured for positioning around an associated leg of the user, such that the associated leg is engaged to the foot rod.

4. The exercise device of claim 1, further including a pair of press bars operationally engaged to and selectively extensible from the chair, each press bar being operationally engaged to a respective biaser, such that the respective biaser is positioned for resisting movement of the press bar relative to the chair, wherein the press bars are configured for exercising arms and shoulders of the user.

5. The exercise device of claim 4, wherein:
   the press bar comprises:
      a press rod slidably engaged to and selectively extensible from a respective opposing side tube of the backrest, and
      a handle engaged to and extending arcuately from the press rod, such that the handle is positioned over an associated shoulder of the user; and
   a respective biaser being positioned in and engaged to the respective opposing side tube, the respective biaser being operationally engaged to the press rod.

6. The exercise device of claim 1, further including a headrest engaged to the backrest distal from the seat, wherein the headrest is configured for supporting a head of the user.

7. The exercise device of claim 6, further including a pair of panels, each panel being hingedly engaged to a respective opposed edge of the headrest, such that the pair of panels is selectively hingable into abutment with the head of the user.

8. The exercise device of claim 1, further including a pair of extensions, each extension being engaged to a respective rear leg, the extension being distal from the seat and extending opposingly from the respective rear leg relative to the seat, wherein the extensions are configured for engaging the substantially horizontal surface for resisting tilting of the chair.

9. The exercise device of claim 1, further including a safety belt engaged to the backrest and being configured for positioning around the abdomen of the user, such that the user is engaged to the chair.

10. The exercise device of claim 1, wherein the footrests are hingedly engaged to the seat, such that the pair of footrests is selectively positionable in a stowed configuration, wherein the footrests are positioned below the seat, and a deployed configuration, wherein the footrests extend transversely from the seat.

11. The exercise device of claim 1, further including a pair of armrests, each armrest being engaged to and extending between a respective front leg and an associated opposing side tube.

12. The exercise device of claim 1, further including:
   a power cord engaged to and extending from the chair, the power cord being operationally engaged to the plurality of heating elements, wherein a plug of the power cord is configured for selectively engaging an outlet for operationally engaging the plurality of heating elements to a source of electrical current; and
   a controller engaged to the chair and being operationally engaged to the power cord and the plurality of heating elements, such that the controller is positioned for selectively operationally engaging a respective heating element to the power cord for powering the respective heating element.

13. An exercise device comprising:
   a chair comprising:
      a seat,
      a pair of front legs and a pair of rear legs engaged to and extending from the seat, wherein the front legs and the rear legs are configured for supporting the seat on a substantially horizontal surface, wherein the seat is configured for seating the user, the front legs extending past the seat,
      a pair of crossbeams, each crossbeam being engaged to and extending between a respective rear leg and an associated front leg, a backrest engaged to and extending from the seat proximate to the rear legs, wherein the backrest is configured for supporting a back of the user, the backrest comprising:
  a pair of opposing side tubes, each opposing side tube being engaged to and extending from a respective rear leg, and
  a back panel engaged to and extending between the opposing side tubes,
a pair of extensions, each extension being engaged to a respective rear leg, the extension being distal from the seat and extending opposingly, from the respective rear leg relative to the seat, wherein the extensions are configured for engaging the substantially horizontal surface for resisting tilting of the chair, and
a safety belt engaged to the backrest and being configured for positioning around the abdomen of the user, such that the user is engaged to the chair;
a plurality of biasers operationally engaged to the chair, each Maser comprising a spring;
a pair of footrests operationally engaged to the chair, each footrest being configured for engaging an associated foot of the user, the footrest being operationally engaged to a respective biaser, such that the respective biaser is positioned for resisting movement of the footrest relative to the chair, wherein the footrests are configured for exercising feet of the user, the footrests being hingedly engaged to the seat, such that the pair of footrests is selectively positionable in a stowed configuration, wherein the footrests are positioned below the seat, and a deployed configuration, wherein the footrests extend transversely from the seat, each footrest comprising:
  a foot rod engaged to and extending from a front edge of the seat,
  a footpad hingedly engaged to the foot, rod distal from the seat,
  and
  a strap engaged to the foot rod and being configured for positioning around an associated leg of the user, such that the associated leg is engaged to the foot rod;
a pair of handrests operationally engaged to the chair, each handiest being configured for engaging an associated hand of the user, the handiest being operationally engaged to a respective biaser, such that the respective biaser is positioned for resisting movement of the handiest relative to the chair, wherein the handrests are configured for exercising hands of the user, the handiest comprising:
  a hand rod slidably engaged to and selectively extensible from a respective front leg of the chair,
  a handpad engaged to the hand rod, and
  a respective biaser being positioned in and engaged to the respective front leg, the respective biaser being operationally engaged to the hand rod;
a pair of armrests, each armrest being engaged to and extending between a respective front leg and an associated opposing side tube;
a plurality of heating elements engaged to the chair, the footrests, and the handrests, wherein the heating elements are configured for warming an abdomen and joints of the user;
a pair of press bars operationally engaged to and selectively extensible from the chair, each press bar being operationally engaged to a respective biaser, such that the respective biaser is positioned for resisting movement of the press bar relative to the chair, wherein the press bars are configured for exercising arms and shoulders of the user, the press bar comprising:
  a press rod slidably engaged to and selectively extensible from a respective opposing side tube of the backrest,
  a handle engaged to and extending arcuately from the press rod, such that the handle is positioned over an associated shoulder of the user, and
  a respective biaser being positioned in and engaged to the respective opposing side tube, the respective biaser being operationally engaged to the press rod:
a headrest engaged to the backrest distal from the seat, wherein the headrest is configured for supporting a head of the user;
a pair of panels, each panel being hingedly engaged to a respective opposed edge of the headrest, such that the pair of panels is selectively hingable into abutment with the head of the user;
a power cord engaged to and extending fro the chair, the power cord being operationally engaged to the plurality of heating elements, wherein a plug of the power cord is configured for selectively engaging an outlet for operationally engaging the plurality of heating elements to a source of electrical current; and
a controller engaged to the chair and being operationally engaged to the power cord and the plurality of heating elements, such that the controller is positioned for selectively operationally engaging a respective heating element to the power cord for powering the respective heating element.

\* \* \* \* \*